United States Patent [19]

Job

[11] Patent Number: 5,229,344
[45] Date of Patent: Jul. 20, 1993

[54] OLEFIN POLYMERIZATION CATALYST

[75] Inventor: Robert C. Job, Houston, Tex.

[73] Assignee: Shell Oil Company, Houston, Tex.

[21] Appl. No.: 905,612

[22] Filed: Jun. 29, 1992

Related U.S. Application Data

[62] Division of Ser. No. 599,539, Oct. 18, 1990, Pat. No. 5,162,277.

[51] Int. Cl.$^5$ .............................................. C08F 4/654
[52] U.S. Cl. ...................................... 502/171; 502/120; 502/124; 502/125; 526/124
[58] Field of Search ................. 502/120, 124, 125, 171

[56] References Cited

U.S. PATENT DOCUMENTS

| | | |
|---|---|---|
| 4,330,649 | 5/1982 | Kioka et al. ................ 502/125 X |
| 4,439,539 | 3/1984 | Takitani et al. ............. 502/125 X |
| 4,472,521 | 9/1984 | Band ............................ 502/124 X |
| 4,525,558 | 6/1985 | Takitani et al. ............. 526/144 |
| 4,540,679 | 9/1985 | Arzoumanidis .............. 502/125 X |
| 4,710,482 | 12/1987 | Job ............................... 502/125 X |
| 4,728,705 | 3/1988 | Nestlerode et al. .......... 526/124 |
| 4,771,024 | 9/1988 | Nestlerode et al. .......... 502/124 X |

*Primary Examiner*—Patrick P. Garvin
*Attorney, Agent, or Firm*—Otto O. Meyers, III

[57] ABSTRACT

An improved high activity olefin polymerization catalyst catalyzes the production of polymeric lower α-olefin having good properties and a relatively narrow particle size distribution. The catalyst is produced from an organoaluminum cocatalyst, a selectivity control agent and a novel olefin polymerization procatalyst which is prepared by contacting a tetravalent titanium halide, a halohydrocarbon, an electron donor and the solid procatalyst precursor obtained by heating an adduct of a carbonated magnesium ethoxide and a phenolic compound of enhanced acidity.

9 Claims, No Drawings

OLEFIN POLYMERIZATION CATALYST

This is a division, of application Ser. No. 07/599,539, filed Oct. 18, 1990 and now U.S. Pat. No. 5,162,217.

FIELD OF THE INVENTION

This invention relates to a high activity olefin polymerization catalyst and to a method for the production thereof. More particularly, the invention relates to a magnesium-containing, titanium-containing component of the olefin polymerization catalyst, to the catalyst produced from that component and to the process of polymerizing olefins which employs that catalyst.

BACKGROUND OF THE INVENTION

The production of polymers and copolymers of lower α-olefins, particularly ethylene and propylene, has gained substantial commercial significance. The polymeric products are relatively inexpensive and exhibit a number of commercially useful properties. In the case of the polymerization of ethylene, the process is relatively uncomplicated in that the product type is not influenced by the manner in which the ethylene molecules add to the growing polymeric chain and the product does not exist in stereoisomeric forms.

In the case of the polymerization of propylene, however, the presence of pendant methyl groups on the polymeric chain results in the possibility of several product types depending upon the stereoregularity with which the propylene molecules add to the growing chain. Much, if not most, of the commercial polypropylene is crystalline and results from the stereoregular addition of propylene molecules in a regular head-to-tail manner. Polymer resulting from the addition of propylene units in a random and irregular manner is termed atactic. This amorphous form is less desirable and, if atactic polymer is present in substantial quantities, must be removed as by an extraction step in order to provide the more desirable crystalline polymer.

Also significant from a commercial standpoint is the activity of the polymerization catalyst. A number of the early polymerization catalysts, e.g. trivalent titanium, chromium or vanadium catalysts, were of a relatively low activity and the polymeric product contained significant proportions of catalyst residues. The removal of such residues as by a deashing step was required in order to obtain commercially acceptable properties.

The more recent olefin polymerization catalysts are more stereo-regulating and of sufficient catalyst activity so that extraction and/or deashing steps are not required. In the terms now employed conventionally to describe such catalysts, the high activity olefin polymerization catalysts are formed from a procatalyst which typically contains magnesium, titanium and halogen moieties, a cocatalyst which is typically an organoaluminum compound and a selectivity control agent which may be provided as a partial or a total complex with the cocatalyst. Although each of these components has a significant influence on the polymerization process and the polymer product produced thereby, the nature of the catalyst as well as the polymer product seems to be most influenced by the particular nature of the procatalyst. Much of the research directed toward improvement of the olefin polymerization catalyst has been devoted to improvement of the procatalyst.

Kioka et al, U.S. Pat. No. 4,330,649, describe a solid catalyst component (procatalyst) obtained by heating a soluble magnesium compound such as magnesium chloride with a higher alcohol in the presence of an ester to produce a solution. This solution is added to titanium tetrachloride and an electron donor to form the procatalyst. Band, U.S. Pat. No. 4,472,521, reacts a magnesium alkoxide with excess titanium alkoxide, wherein each alkoxide has 4 or more carbons in the presence of aromatic hydrocarbon. Titanium tetrachloride and an electron donor are added to the resulting solution to produce a solid procatalyst which is posttreated with transition metal halide.

A number of the more attractive olefin polymerization procatalysts are produced from magnesium alkoxides wherein the alkoxide moieties have one or two carbon atoms. Magnesium ethoxide appears to be a particularly attractive procatalyst precursor. The use of magnesium ethoxide poses a somewhat unique problem in that, unlike other magnesium alkoxides, magnesium ethoxide is not readily soluble in the corresponding alkanol, i.e., ethanol. Various measures have been proposed for the solubilization of magnesium alkoxide including the formation of complex magnesium ethoxides as disclosed by Job, U.S. Pat. No. 4,710,482.

Several procedures have been disclosed which involve the solubilization of magnesium ethoxide by reaction with carbon dioxide in ethanol. Arzoumanidis, U.S. Pat. No. 4,540,679, produces an olefin polymerization catalyst component by contacting a suspension of magnesium ethoxide in ethanol with carbon dioxide. To the resulting solution is added an organoaluminum compound in hydrocarbon solution to produce granular particles which are employed as a support for the titanium species which result from contacting the granular particle with titanium tetrachloride. Nestlerode et al, U.S. Pat. No. 4,728,705, react magnesium ethoxide in ethanol with carbon dioxide to form a solution. This solution is spray dried to produce particles or alternatively is used to impregnate carrier particles. The particles resulting from either modification are useful in the production of an olefin polymerization procatalyst of particularly desirable morphology.

The reaction of magnesium ethoxide with carbon dioxide in ethanol produces a soluble complex containing moieties of magnesium, ethoxide and carbon monoxide which is often referred to as carbonated magnesium ethoxide or CMEO. The precise structure of the complex is somewhat uncertain but a low pressure stable form is believed to the illustrated by the formula

$$Mg_2(OEt)_4(CO_2)_3 \qquad (I)$$

and the complex is soluble in ethanol. Although the above references teach methods of converting this carbon dioxide-containing complex to olefin polymerization procatalysts and thence to olefin polymerization catalysts, it would be of advantage to provide improved olefin polymerization procatalysts and catalysts from the carbonated magnesium ethoxide complex.

SUMMARY OF THE INVENTION

The present invention relates to an improved olefin polymerization catalyst and to a process of polymerizing lower α-olefins in the presence of such catalyst. More particularly, the invention relates to a procatalyst precursor of such olefin polymerization catalyst and to the production thereof from carbonated magnesium ethoxide.

DESCRIPTION OF THE INVENTION

The present invention contemplates the production of an olefin polymerization procatalyst precursor by reaction of carbonated magnesium ethoxide and certain phenolic compounds of enhanced acidity. The resulting spheroidal solid is heated in an inert diluent to produce, as a new solid material, the polymerization procatalyst precursor. The precursor is contacted with tetravalent titanium halide, halohydrocarbon and an electron donor to produce the procatalyst as solid, spheroidal particles. Contacting the procatalyst with organoaluminum compound cocatalyst and a selectivity control agent produces the olefin polymerization catalyst which is useful in the polymerization of lower α-olefins to polymeric product having a relatively narrow particle size distribution and good properties.

The production of a carbonated magnesium ethoxide solution in ethanol is known in the art, inter alia, from the disclosures of the above U.S. Pat. Nos. 4,540,679 and 4,728,705 references. In general, the process of producing the carbonated magnesium ethoxide solution comprises the passing of carbon dioxide into a slurry of magnesium ethoxide in ethanol as by bubbling the gaseous carbon dioxide through the slurry or by adding dry ice. The magnesium ethoxide is "solubilized" by interaction with the carbon dioxide and ethanol, probably through the formation of a complex carbonated alcoholate of the general formula $$Mg(OEt)_2(CO_2)_x \qquad (II)$$

wherein x is an average number between 1 and about 2 inclusive. The carbonated complex is soluble in ethanol and the course of the interaction is followed by observing the disappearance of the insoluble magnesium ethoxide.

The carbonated magnesium ethoxide is then contacted with a phenolic compound selected from phenol or a substituted phenol whose acidity has been enhanced by the presence of an electron withdrawing group as a substituent on a phenolic ring carbon atom. The class of electron withdrawing groups is well recognized in the art and generally comprises those groups whose presence as an aromatic ring substituent causes sufficient electron withdrawal such as to reduce the pKa of the substituted phenolic compound, in aqueous solution, below a value of about 9.9. As is recognized in the art the class of electron withdrawing groups as conventionally constituted includes those electron withdrawing groups which are suitable ring substituents on the phenolic compounds of enhanced acidity of the invention such as nitro, cyano, chloro, bromo, carboxy, carboalkoxy, formyl and alkoxy, but does not include hydroxy or alkyl. The preferred electron withdrawing groups are free of active hydrogens and particularly preferred as the electron withdrawing, meta-directing substituent is the nitro group.

The suitable phenolic compounds of enhanced acidity have from 1 to 2 aromatic rings with from 1 to 2 electron withdrawing groups as above described which are preferably located on ring carbon atoms which are ortho or para relative to the phenolic hydroxyl group. Such suitable phenolic compounds include o-nitrophenol, p-nitrophenol, p-chlorophenol, p-hydroxybenzaldehyde, 2-ethoxyphenol, p-cyanophenol, 4-carbethoxyphenol, 4-acetyloxyphenol, 2-carbomethoxyphenol, 2,4-dinitrophenol, 2-nitro-1-hydroxynaphthalene and 4-cyano-1-hydroxynaphthalene. Preferred phenols of enhanced acidity have one aromatic ring and one substituent group and are nitrophenols, particularly p-nitrophenol.

The carbonated magnesium ethoxide and the phenolic compound are contacted at a moderate temperature in an inert reaction diluent in which the carbonated magnesium ethoxide and phenolic compound are soluble but the reaction product thereof is insoluble. Suitable diluents include the alkanols, especially ethanol, aromatic hydrocarbons such as benzene, toluene and xylene, aromatic halohydrocarbons such as chlorobenzene, dichlorobenzene and bromobenzene, alkyloxysilanes including tetramethoxysilane, tetraethoxysilane and trimethoxypropoxysilane, and mixtures thereof. Alkanols are preferred as the diluents.

The contacting takes place at a temperature at or about ambient, e.g., from about 15° C. to about 30° C., and the mixing is facilitated by conventional procedures such as shaking or stirring. The resulting product is a granular solid, insoluble in the medium of its production. This granular solid is an adduct of the carbonated magnesium ethoxide and a moiety of the phenolic compound and is of the general formula $$Mg(O_2C)(OEt)(A).EtOH \qquad (IV)$$

wherein A is the phenoxide anion illustratively obtained by loss of the phenolic hydrogen from the phenolic compound of enhanced acidity.

The olefin polymerization procatalyst precursor is obtained by heating the granular solid in a high boiling inert diluent. This diluent is suitably a high boiling diluent, i.e., a diluent which has an atmospheric boiling point above about 80° C. and preferably above about 100° C. The aromatic halohydrocarbons and the tetraalkoxysilanes are preferred. In one modification, the granular solid is heated in the diluent of its production until effervescence takes place. In an alternate modification, particularly useful when a relatively low boiling diluent is employed in the production of the granular solid, the solid is recovered from the medium of its production as by filtration or decantation, mixed with the high boiling diluent and heated until effervescence takes place. The effervescence which takes place in either modification results from the loss of at least a portion of the carbon dioxide and/or ethanol present in the carbonated magnesium ethoxide/phenolic compound adduct. When the effervescence has diminished or ceased altogether, the resulting solid procatalyst precursor is recovered as by filtration or decantation. This solid procatalyst precursor is typically washed with a light hydrocarbon such as isooctane and dried, although the recovered solid may be used in the production of procatalyst without additional treatment.

The olefin polymerization procatalyst is produced by contact of the solid procatalyst precursor with a tetravalent titanium halide, an optional halohydrocarbon and an electron donor. The tetravalent titanium halide is suitably an aryloxy- or alkoxy- di- or tri-halide such as diethoxytitanium dichloride, dihexyloxytitanium dibromide, isopropoxytitanium trichloride or phenoxytitanium trichloride or the tetravalent titanium halide is a titanium tetrahalide such as titanium tetrachloride or titanium tetrabromide. A titanium tetrahalide is preferred as the tetravalent titanium halide and particularly preferred is titanium tetrachloride.

The optional halohydrocarbon employed in the production of the olefin polymerization procatalyst is a halohydrocarbon of up to 12 carbon atoms inclusive, preferably of up to 9 carbon atoms inclusive, which contains at least one halogen atom, preferably chlorine or bromine, and in the case of aliphatic halohydrocarbons contains at least 2 halogen atoms. Exemplary aliphatic halophydrocarbons are methylene chloride, methylene bromide, chloroform, carbon tetrachloride, 1,2-dibromoethane, 1,1,3-trichloropropane, trichlorocyclohexane, dichlorofluoromethane and tetrachloroisooctane. Suitable aromatic halohydrocarbons include chlorobenzene, bromobenzene, dichlorobenzene and chlorotoluene. Of the aliphatic halohydrocarbons, carbon tetrachloride and 1,1,2-trichloroethane are preferred but particularly preferred is the aromatic halohydrocarbon chlorobenzene.

The electron donors which are suitably included within the procatalyst are the generally conventional electron donors employed in titanium-based olefin polymerization procatalysts including ethers, esters, ketones, amines, imines, nitriles, phosphines, stibines, arsines and alcoholates. The preferred electron donors are esters and particularly aliphatic esters of aromatic monocarboxylic or dicarboxylic acids. Examples of such preferred electron donors are methyl benzoate, ethyl benzoate, ethyl p-ethoxybenzoate, ethyl p-methylbenzoate, diethyl phthalate, diisobutyl phthalate, diisopropylterephthalate and dimethyl naphthalenedicarboxyate. The electron donor is a single compound or a mixture of two or more compounds but preferably the electron donor is provided as a single compound. Of the preferred ester electron donors, ethyl benzoate and diisobutyl phthalate are particularly preferred.

The manner by which the solid procatalyst precursor, tetravalent titanium halide, the halohydrocarbon and the electron donor are contacted is material but not critical and is generally conventional. In one modification the procatalyst precursor and the tetravalent titanium halide are mixed and the electron donor is subsequently added to the resulting mixture. In a preferred modification, the electron donor and procatalyst precursor are mixed with a mixture of tetravalent titanium halide and halohydrocarbon and the resulting solid is washed one or more additional times with the mixture of tetravalent titanium halide and halohydrocarbon. The initial contacting of electron donor, procatalyst precursor and tetravalent titanium halide/halohydrocarbon mixture is suitably conducted at a temperature from about ambient to about 150° C. Better interaction of these materials is obtained if they are heated and initial contacting temperatures from about 80° C. to about 130° C. are preferred. Sufficient tetravalent titanium halide is employed to convert at least a substantial proportion of the anions of the solid procatalyst precursor to halide moieties. This conversion, frequently referred to as halogenation, is conducted in one or more operations, each of which is conducted over a period of time ranging from a few minutes to several hours. During each contacting with tetravalent titanium halide a portion of the halohydrocarbon is typically present and halogenation is facilitated on some occasions by the additional presence of an acid halide such as benzoyl chloride or phthaloyl chloride. Sufficient electron donor is provided so that the molar ratio of electron donor to magnesium in the procatalyst precursor is from about 0.01:1 to about 10:1, preferably from about 0.06:1 to about 0.4:1. The solid procatalyst, obtained as spherical particles, is typically finished by a final wash with light hydrocarbon and drying under nitrogen. The procatalyst so obtained is storage stable so long as oxygen and active hydrogen compounds are excluded. Alternatively, however, the procatalyst is used as obtained directly from the hydrocarbon wash without the need for drying. The procatalyst is used in the production of olefin polymerization catalyst by contact of the procatalyst with organoaluminum cocatalyst an d a selecgtivity control agent.

The cocatalyst is an organoaluminum compound which is selected from the aluminum-based cocatalysts conventionally employed with titanium-based procatalysts. Illustrative organoaluminum compounds are trialkylaluminum compounds, alkylaluminum alkoxide compounds and alkylaluminum halide compounds wherein each alkyl independently has from 2 to 6 carbon atoms inclusive. The preferred organoaluminum compounds are halide free and particularly preferred are the trialkylaluminum compounds such as triethylaluminum, triisobutylaluminum, triisopropylaluminum and diethylhexylaluminum. Triethylaluminum is the preferred member of the class of trialkylaluminum compounds. The cocatalyst is employed in a sufficient quantity to provide a ratio of aluminum atoms to titanium atoms in the procatalyst from about 1:1 to about 150:1 but preferably from about 10:1 to about 100:1.

The selectivity control agents which are employed in the production of the olefin polymerization catalyst are those conventionally employed in conjuction with titanium-based procatalysts and organoaluminum cocatalysts. Suitable selectivity control agents include those electron donors as listed above for use in procatalyst production but also include organosilane compounds including alkylalkoxysilanes and arylalkoxysilanes of the formula

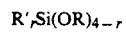

wherein R' is alkyl or aryl of up to 10 carbon atoms inclusive, R is lower alkyl of up to 4 carbon atoms and r is 1 or 2. The preferred selectivity control agents are esters and particularly alkyl esters of aromatic monocarboxylic and dicarboxylic acids or are alkylalkoxysilanes. Illustrative of the preferred esters are ethyl p-ethoxybenzoate, diisobutyl phthalate, ethyl benzoate and ethyl p-methylbenzoate and the preferred alkylalkoxysilanes include diisobutyldimethoxysilane, isopropyltrimethoxysilane and cyclohexylmethyldimethoxysilane. The selectivity control agent is provided in a quantity sufficient to provide from about 0.01 mole to about 100 moles per mole of titanium in the procatalyst, preferably from about 0.5 mole to about 20 moles per mole of titanium in the procatalyst. The selectivity control agent is typically provided as a separate material at the time the catalyst is formed but alternatively in certain embodiments the electron donor provided during procatalyst production may also serve as selectivity control agent without the addition of additional material.

The components of the olefin polymerization catalyst are usefully contacted by mixing in a suitable reactor outside the system in which lower α-olefin is to be polymerized and the catalyst thereby produced is subsequently introduced into the polymerization reactor. Alternatively, however, the catalyst components are introduced separately into the polymerization reactor where the olefin polymerization catalyst is formed in situ.

The olefin polymerization catalyst as formed from the carbonated magnesium ethoxide/phenolic compound adduct by way of the solid procatalyst is useful in the polymerization of lower α-olefins and particularly in the polymerization of straight-chain α-olefins of up to 4 carbon atoms inclusive, i.e., ethylene, propylene or 1-butene. The precise procedures of polymerization are broadly conventional but the olefin polymerization of the invention, by virtue of the use therein of the polymerization catalyst formed ultimately from the carbonated magnesium ethoxide/phenolic compound adduct, provides polymeric product having good properties including a relatively high bulk density and moreover is obtained in the form of particles of a relatively narrow particle size distribution. The activity and stereospecificity of the catalyst are such that the polymeric product of desirable properties is obtained without the need for a deashing or an extraction step.

The polymerization product is suitably a homopolymer as when a single α-olefin monomer is provided to the polymerization process. Alternatively, the process is useful for the production of copolymers or terpolymers as when two or more α-olefins are provided to the polymerization process of the invention such as in the production of EPR or polypropylene impact copolymers.

The polymerization is conducted under polymerization conditions as a gas-phase process employing one or more fluidized beds of catalyst or the polymerization is conducted as a slurry-phase process incorporating as diluent an inert material such as propane or a liquified monomer of the polymerization such as propylene. The process is conducted in a batchwise manner or a continuous or semi-continuous process with constant or intermittent addition of the catalyst, catalyst components and/or α-olefin to the polymerization reactor. During the polymerization, the molecular weight and to some extent the properties of the polymer product will be influenced by the provision of molecular hydrogen as is known in the art.

The invention is further illustrated by the following Illustrative Embodiments which should not be construed as limiting.

ILLUSTRATIVE EMBODIMENT I

In an 8-ounce bottle were mixed 87.25 g of a carbonated magnesium ethoxide solution in ethanol containing 125 mmol of magnesium and 3.65 g of tetraethoxysilane. To the solution as it was stirred was added 17.38 g (125 mmol) of 4-nitrophenol dissolved in 17.4 g of ethanol. After stirring overnight at room temperature, the resulting slurry was filtered and the solids were washed with isooctane and dried under flowing nitrogen. The yield was 33.6 g of yellow granular crystals in the 2-14 micron range. A portion of that solid, 20 g, was added to 150 g of chlorobenzene and the mixture was boiled for about 1 hour while placed in a 164° C. oil bath. The resulting solid was recovered by filtration, washed with isooctane and dried under nitrogen. This second solid was more orange than was the solid before boiling.

ILLUSTRATIVE EMBODIMENT II

To 90.8 g of a carbonated magnesium ethoxide solution in ethanol (125 mmol Mg) was added 17.4 g (125 mmol) of 4-nitrophenol. After precipitation had begun the mixture was stirred at 60° C. for 2 hours and then allowed to cool to room temperature. The resulting solid was recovered by filtration, washed with isooctane and dried under nitrogen. The yield was 28.7 g of crystalliine particles having a size within the 15-20 micron range. A portion of those particles, 18.4 g, was added to 225 g tetraethoxysilane and the mixture was stirred for about 1 hour at 80° C. and then heated to near boiling while being stirred for an additional 7 hours. The resulting solid was recovered by filtration, washed with isooctane and dried under flowing nitrogen. The yield of solid was 14 g.

ILLUSTRATIVE EMBODIMENT III

Magnesium ethoxide (350 g, 3.06 mole) was mixed with 1113 g of ethanol containing 84.6 g of tetraethoxysilane and then dry ice chunks were added until a clear solution was obtained. To the solution while it was stirred was added 353.5 g (2.54 mole) of 4-nitrophenol dissolved in 320 g of ethanol. The mixture was stirred at 400-500 rpm overnight at room temperature. Two crops of solid were collected, washed once with ethanol, then with isooctane and dried under flowing nitrogen. The yield of spheroidal particles was 728.2 g (96%) and the particles were found to be in the 3-8 micron size range.

A. One procatalyst precursor was prepared by first boiling 20 g of the spheroidal particles in 150 g of chlorobenzene to produce 15.9 g of powder. An 11.1 g portion of that powder was boiled in 131 g of tetraethoxysilane to produce 9.4 g of a second powder.

B. A second procatalyst precursor was produced by boiling 20.67 g of the spheroidal particles for about one hour in 200 g of tetraethoxysilane. A yield of 15.6 g of a second powder was obtained.

ILLUSTRATIVE EMBODIMENT IV

Each procatalyst precursor product of Illustrative Embodiments I, II, IIIA and IIIB was stirred with diisobutyl phthalate in a volume of 60 ml of a 50/50 by volume mixture of titanium tetrachloride/chlorobenzene for every 50 milliequivalents of magnesium precursor for 1 hour at 115° C. The resulting mixture was filtered while hot and the solids recovered thereby were washed twice with fresh 60 ml portions of the 50/50 mixture. The solids were then rinsed once with 125 ml of isooctane at 90° C. and twice with isooctane at room temperature, and then dried overnight under flowing nitrogen. The proportions of procatalyst precursor and diisobutyl phthalate and the elemental composition of each procatalyst are shown in Table I wherein "Ratio" indicates the milliliters of diisobutyl phthalate used and the weight of procatalyst precursor in grams.

TABLE I

| Precursor from Illustrative Embodiment | Ratio (ml/gms) | Composition, % wt. | | |
|---|---|---|---|---|
| | | Ti | Mg | Cl |
| I | 0.85/4.5 | 9.98 | 8.98 | 48.2 |
| II | 0.85/4.6 | 7.90 | 7.90 | 39.4 |
| IIIA | 0.57/2.3 | 5.07 | 14.8 | 52.9 |
| IIIB | 0.85/4.3 | 8.67 | 9.97 | 49.6 |

ILLUSTRATIVE EMBODIMENT V

Each procatalyst produced by the procedure of Illustrative Embodiment IV was converted to an olefin polymerization catalyst by mixing with triethyl aluminum cocatalyst and diisobutyldimethoxysilane as selectivity control agent. The catalysts were employed to polymerize propylene in a slurry-phase process in liquid propylene as diluent. The polymerizations took place in a 1 gallon autoclave for 1 hour at 67° C. with 43 mmol of added hydrogen. The catalyst components were mixed in proportions to give an Al/Si/Ti molar ratio of 70/20/1. The mixing took place 20 minutes prior to the injection of the catalyst into the autoclave which had been heated to about 65° C. The results of these polymerizations are shown in Table II where "Productivity" refers to the yield of polypropylene polymer in kg of polymer/g of catalyst/hour . The term "BD" refers to bulk density of the polymer in g/cc. The stereospecificity of the catalyst is measured by determining the percent by weight of xylene solubles (termed XS) is accordance with the regulations of the U.S. Food and Drug Administration. This test is conducted by dissolving a polymer sample in xylene under reflux in a flask. The flask is then immersed in a water bath at 25° C. for 1 hour without stirring. During this time the insoluble portion precipitates and is then removed by filtration. An aliquot of the filtrate is evaporated, dried and weighed to enable calculation of the overall xylene solubles content. The xylene soluble portion consists primarily of amorphous (atactic) polymer with a small amount of low molecular weight crystalline polymer.

TABLE II

| Polymerization | Precursor Source of Catalyst | Productivity | XS | BD |
|---|---|---|---|---|
| 1 | I | 16.5 | 3.7 | 0.33 |
| 2 | | 18.9*** | 3.2 | 0.365 |
| 3 | II | 15.7 | 4.0 | 0.415 |
| 4 | | 14.2 | 3.1 | 0.45 |
| 5 | IIIA | 11.3 | sticky | 0.399 |
| | | ** | | 0.434 |
| 6 | | 32.6 | sticky | 0.370 |
| | | ** | | 0.438 |
| 7 | IIIB | 17.2 | — | 0.365 |
| 8 | | 19.6* | 3.4 | 0.365 |

*Twice as much triethylaluminum used.
**The sticky polymer was washed with isooctane and the BD re-measured.
***Additional silane employed in polymerization reaction.

ILLUSTRATIVE EMBODIMENT VI

The particle size distribution of the polymers produced by polymerizations conducted according to the procedure of Illustrative Embodiment V was determined by standard ASTM procedure by shaking in a set of wire sieves and compared with that obtained by use of a standard polypropylene catalyst wherein the procatalyst was produced from magnesium ethoxide. The results are shown in Table III wherein WAPS refers to the weight average particle size in microns, the term "mesh" followed by a number indicates the percentage of the particles retained by a wire mesh screen having openings equal to that number in size measured in microns, and range refers to the ratio of weight percent on the largest screen shown to the weight percent on the smallest shown, for each sample. The major distributions of size are indicated and the total for that range indicated in the final column, but all samples of polymer contained smaller proportions of particles of other sizes.

It is to be noted that all of the polymers produced according to this invention had the major portion (>86%) of the particles in a narrow size range ratio of about 2 whereinas 84% of the polymer obtained from the comparative example, obtained by use of a catalyst having a more conventional procatalyst, occurred in a very broad size range ratio of 8.7.

TABLE III

| Polymerization Procedure | WAPS | Mesh | Range | % in Range |
|---|---|---|---|---|
| 2 | 315 | 35%–400 | 1.7 | 86 |
| | | 31%–300 | | |
| | | 15%–263 | | |
| | | 5%–236 | | |
| 3 | 549 | 30%–750 | 1.9 | 97 |
| | | 31%–575 | | |
| | | 24%–500 | | |
| | | 12%–400 | | |
| 5 | 225 | 3%–200 | 1.7 | 94 |
| | | 43%–263 | | |
| | | 38%–236 | | |
| | | 10%–175 | | |
| 6 | 306 | 43%–400 | 1.7 | 91 |
| | | 32%–300 | | |
| | | 12%–263 | | |
| | | 4%–236 | | |
| 8 | 223 | 13%–400 | 2.3 | 86 |
| | | 6%–300 | | |
| | | 8%–263 | | |
| | | 12%–236 | | |
| | | 47%–175 | | |
| Comparative | 678 | 38%–1500 | 8.6 | 84 |
| | | 25%–750 | | |
| | | 13%–425 | | |
| | | 8%–175 | | |

ILLUSTRATIVE EMBODIMENT VII

In each of the examples shown below (Table IV), 125 mmol of an ethanol solution of the indicated phenol was added to 125 mmol of an ethanol solution of Mg(O-Et)$_2$.1.55 CO$_2$ (prepared as in the above embodiment). In some cases CO$_2$ evolution was evident and a precipitate was formed. In other cases there was no gas evolution and no precipitate formed. Table V shows literature values of relative acidities of some substituted phenols in aqueous solution. On the basis of the observations shown, the phenols used in the examples of this invention can be grouped into the two categories, (1) the phenolic compounds of the invention, and substituted phenols containing strongly electron withdrawing substituents; (2) those substituted phenols which contained the groups which would be expected to produce lower acidity (—CH$_3$, —OH), did not react with the solution to evolve CO$_2$ and did not produce precipitate.

TABLE IV

| Phenol | Observation |
|---|---|
| Hydroquinone (4-hydroxyphenol) | No gas evolution at room temperature, no gas evolution at 80°, no precipitate |
| Resorcinol (3-hydroxyphenol) | No gas evolution, no precipitate |
| p-cresol (4-methylphenol) | No precipitate at room temperature, no precipitate at 80° |
| 2-methylresorcinol | No CO$_2$ evolution, no precipitate |
| Phenol | Short heating gave gas evolution and a white paste |
| 4-chlorophenol | Slow effervescence at room temperature |
| 2-nitroresorcinol | Vigorous foaming, massive flocculant blue precipitate |
| 4-hydroxybenzaldehyde | Effervescence and formation of 5-8 micron crystalline granules |
| 2-ethoxyphenol | Vigorous foaming, white pasty precipitate |
| 4-methoxyphenol | No precipitate at room temperature, effervescence and voluminous |

TABLE IV-continued

| Phenol | Observation |
|---|---|
| | precipitate at 78° C. |

TABLE V

| Phenol Compound | pKa |
|---|---|
| 4-nitrophenol | 7.15 |
| 4-chlorophenol | 9.18 |
| Phenol | 9.89 |
| 4-methylphenol | 10.17 |
| 4-hydroxyphenol | 10.35 |

What is claimed is:

1. A granular magnesium-containing solid comprising the reaction product of a carbonated magnesium ethoxide and a phenolic compound of enhanced acidity of from 1 to 2 aromatic rings and from 1 to 2 electron withdrawing groups as ring carbon atom substituents.

2. The solid reaction product of claim 1 of the formula

Mg(O₂C)(OEt)(A).EtOH wherein A is the anion of the phenolic compound.

3. The solid reaction product of claim 2 wherein A is the anion of a nitrophenol.

4. The solid reaction product of claim 3 wherein the nitrophenol is 4-nitrophenol.

5. The solid reaction product of claim 2 wherein A is the anion of 4-hydroxybenzaldehyde.

6. An olefin polymerization procatalyst precursor obtained by heating a magnesium-containing solid reaction product of a carbonated magnesium ethoxide and a phenolic compound of enhanced acidity of from 1 to 2 aromatic rings and from 1 to 2 electron withdrawing groups as ring carbon atom substituents.

7. The procatalyst precursor of claim 6 wherein the solid reaction product is of the formula Mg(O₂C)(OEt)(A).EtOH wherein A is the anion of the phenolic compound.

8. The procatalyst precursor of claim 9 wherein A is the anion of nitrophenol.

9. The procatalyst precursor of claim 8 wherein the nitrophenol is 4-nitrophenol.

* * * * *